United States Patent [19] [11] 4,393,210
Senda et al. [45] Jul. 12, 1983

[54] 1(2H)-ISOQUINOLONE COMPOUNDS AND ACID ADDITION SALTS THEREOF

[75] Inventors: Shigeo Senda, Gifu; Eiichi Katho, Aza-nishimachi; Osamu Ohtani, Minokamo; Hidekazu Miyake; Khosuke Fujiwara, both of Tokushima, all of Japan

[73] Assignees: Seiyaku Co., Ltd., Aichi; Taiho Pharmaceutical Co., Ltd., Tokyo, both of Japan

[21] Appl. No.: 182,188

[22] Filed: Aug. 28, 1980

[51] Int. Cl.³ .................. C07D 217/14; A61K 31/47
[52] U.S. Cl. .............................. 546/141; 424/248.54; 424/248.55; 424/248.56; 424/250; 424/258; 544/128; 544/363
[58] Field of Search ...................... 546/141, 146, 147; 544/128, 363

[56] References Cited

U.S. PATENT DOCUMENTS 3,600,394 8/1971 Coyne et al. .................. 546/141
4,137,318 1/1979 Eberlein et al. ............... 546/141

Primary Examiner—Donald G. Daus
Assistant Examiner—J. H. Turnipseed
Attorney, Agent, or Firm—Sughrue, Mion, Zinn, Macpeak and Seas

[57] ABSTRACT

1(2H)-Isoquinolone compounds represented by the formula (1)

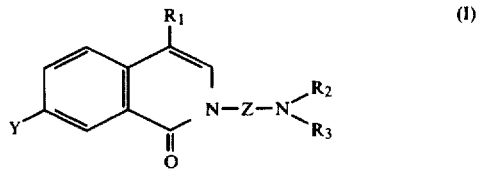

wherein Y represents hydrogen, chlorine or a methoxy group, Z represents a straight chain or branched chain divalent saturated aliphatic hydrocarbon group having 2 to 4 carbon atoms, $R_1$ represents a cyano group, a lower alkoxycarbonyl group, a carbamoyl group, an N-substituted carbamoyl group, a phenyl group or a substituted phenyl group, $R_2$ represents hydrogen or a lower alkyl group, and $R_3$ represents a lower alkyl group, or $R_2$ and $R_3$ can form, when taken together with the nitrogen atom to which they are attached, a heterocyclic group, and the acid addition salts thereof, useful as analgesic, gastric secretion inhibitory, anti-depression, anti-histamine, anti-cholinergic and anti-ulcer agents.

5 Claims, 8 Drawing Figures

1(2H)-ISOQUINOLONE COMPOUNDS AND ACID ADDITION SALTS THEREOF

BACKGROUND OF THE INVENTION

1. Field of the Invention

This invention relates to novel 1(2H)-isoquinolone compounds and the acid addition salts thereof which exhibit useful analgesic, gastric secretion inhibitory, anti-depression, anti-histamine, anti-cholinergic and anti-ulcer activities.

2. Description of the Prior Art

Hitherto, a wide variety of 1(2H)-isoquinolone compounds were known to have various pharmacological activities. For example, U.S. Pat. No. 3,600,394 discloses 2-aminoalkyl-3-substituted-phenyl-1(2H)-isoquinolone having anti-inflammatory and anti-microbial activities; Japanese Patent Publication (Unexamined) No. 122,075/76 and German OLS No. 2,702,600 disclose 7-substituted-3-substituted-phenyl-1(2H)-isoquinolone compounds useful as, e.g., anti-convulsant and anti-hypertensive agent. However, these known compounds are different from the compounds of this invention in their activities and chemical structure.

As a result of extensive studies, the present inventors found novel 1(2H)-isoquinolone compounds represented by the formula (I) useful as analgesic, gastric secretion inhibitory, anti-depression, anti-histamine, anti-cholinergic and anti-ulcer agents.

SUMMARY OF THE INVENTION

The present invention is therefore to provides novel 1(2H)-isoquinolone compounds having the formula (I) hereinafter described and the acid addition salts thereof which are useful as pharmaceutical agents.

DETAILED DESCRIPTION OF THE INVENTION

Figure 1B:
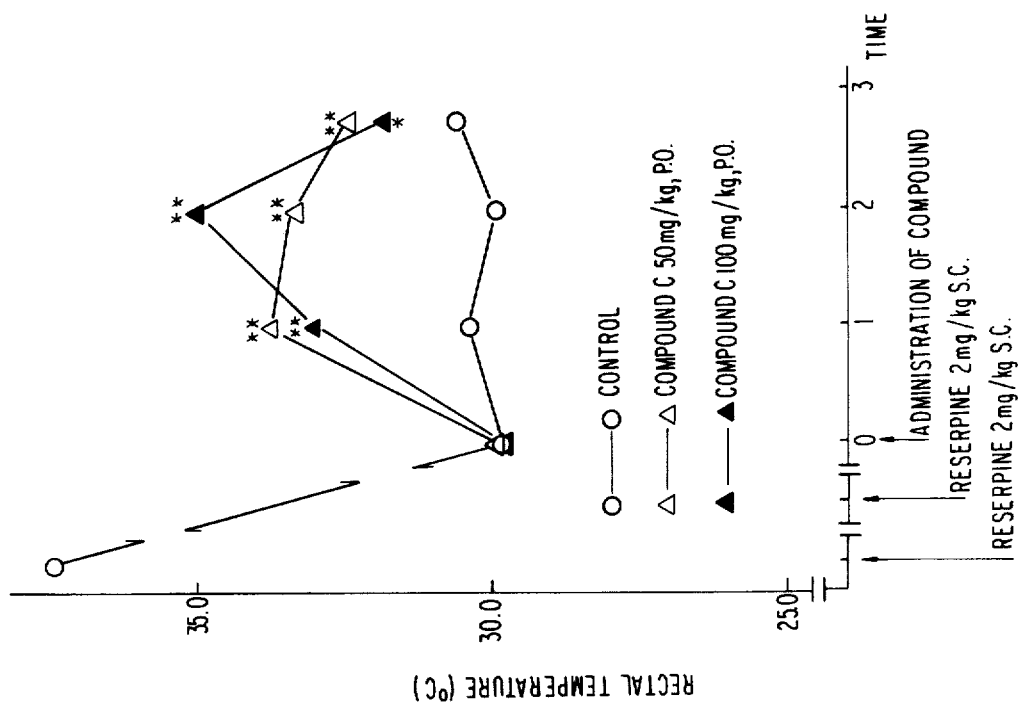
FIGS. 1(a) and 1(b) are graphs showing effects of the known compounds and Compound C of this invention on the decrease in body temperature induced by administration of reserpine.

The 1(2H)-isoquinolone compounds according to the present invention are represented by the formula (I)

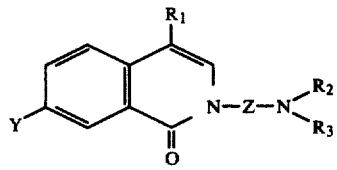
(I)

wherein Y represents hydrogen, chlorine or a methoxy group, Z represents a straight chain or branched chain divalent saturated aliphatic hydrocarbon group having 2 to 4 carbon atoms, $R_1$ represents a cyano group, a lower alkoxycarbonyl group, a carbamoyl group, an N-substituted carbamoyl group, a phenyl group or a substituted phenyl group, $R_2$ represents hydrogen or a lower alkyl group, $R_3$ represents a lower alkyl group, or $R_2$ and $R_3$ can form, when taken together with the nitrogen atom to which they are attached, a heterocyclic group, and the acid addition salts thereof.

The term "a straight chain or branched chain divalent saturated aliphatic hydrocarbon group" as used herein means an alkylene group having 2 to 4 carbon atoms which can be substituted with an alkyl group having 1 to 4 carbon atoms, for example, an ethylene group, a trimethylene group, a methylethylene group, a methyltrimethylene group and the like.

The term "a lower alkoxycarbonyl group" as used herein means an alkoxycarbonyl group having 1 to 4 carbon atoms in the alkoxy moiety such as a methoxycarbonyl group, an ethoxycarbonyl group, propoxycarbonyl groups, butoxycarbonyl groups and the like.

The term "N-substituted carbamoyl group" as used herein means an N-alkylcarbamoyl group, an N,N-dialkylcarbamoyl group wherein each alkyl group has 1 to 4 carbon atoms, a 4-methylpiperazinocarbonyl group, a morpholinocarbonyl group and the like.

The term "substituted phenyl group" as used herein means a halophenyl group such as a p-chlorophenyl group or an alkoxyphenyl group having 1 to 4 carbon atoms in the alkoxy group, for example, a p-methoxyphenyl group.

The term "lower alkyl group" as used herein means a straight chain or branched chain alkyl group having 1 to 4 carbon atoms such as methyl, ethyl, n-propyl, isopropyl, n-butyl, sec-butyl and the like.

Examples of the heterocyclic group formed by $R_2$ and $R_3$ together with the nitrogen atom to which they are attached are a pyrrolidino group, a piperidino group, a 4-methylpiperazino group, a 4-hydroxyethylpiperazino group, a morpholino group, etc.

The term "acid addition salts" as used herein for the compounds of the formula (I) means the salts with pharmaceutically acceptable inorganic or organic acids and preferred examples of the salts are hydrochloride, sulfate, hydrobromide, methanesulfonate, maleate, tartarate, citrate, lactate and the like.

The 1(2H)-isoquinolone compounds of the formula (I) can be prepared by reacting a substituted-1(2H)-isoquinolone having the formula (II)

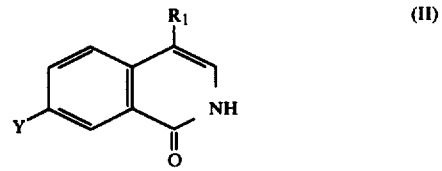
(II)

wherein Y and $R_1$ are as defined above, with a substituted-aminoalkyl halide of the formula (III)

(III)

wherein X represents a halogen atom such as chlorine, bromine and the like and Z, $R_2$ and $R_3$ are as defined above, in the presence of a basic catalyst.

More particularly, the above reaction between the compounds of the formulae (II) and (III) can be advantageously carried out by dissolving the substituted-1(2H)-isoquinolone of the formula (II) in an organic solvent such as dimethylformamide, dimethyl sulfoxide, toluene, ethanol, etc., adding thereto a basic catalyst, for example, alkali metal carbonates such as potassium carbonate, sodium carbonate and the like, sodium hydride, sodium amide, alkali metal alkoxides such as sodium methoxide, sodium ethoxide, potassium t-butoxide and the like, followed by, optionally, heating; then adding to the resulting reaction mixture the substituted aminoalkyl halide of the formula (III) and heating the mixture at a temperature of about 80° to about 140° C. for a period of about 1 to 5 hours.

In the above reaction, the basic catalyst and the substituted aminoalkyl halide can be used in at least an equimolar amount to the substituted 1(2H)-isoquinolone of the formula (II). Also, the substituted aminoalkyl halide (III) can be used in the form of a salt with an inorganic acid such as hydrochloride and the like and, in such instance, the basic catalyst is preferably used in a slightly excess amount over the equimolar amount to the compound (II).

Most of the substituted aminoalkyl halide of the formula (III) are commercially available, but when the desired aminoalkyl halides are not available, the compounds of the formula (I) can also be prepared from the substituted 1(2H)-isoquinolone of the formula (II) via an alternative route using an amine according to the following procedures. That is, the compounds of the formula (I) can be prepared by reacting the compound of the formula (II) with a hydroxyalkyl halide of the formula (IV)

wherein X and Z are as defined above, to produce the corresponding 2-(hydroxyalkyl)-1(2H)-isoquinolone compound of the formula (V)

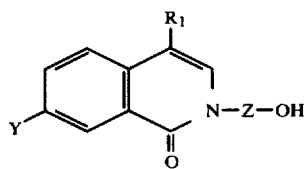

wherein Y, Z and $R_1$ are as defined above, reacting the compound of the formula (V) with a halogenating agent to produce a 2-(haloalkyl)-1(2H)-isoquinolone compound of the formula (VI)

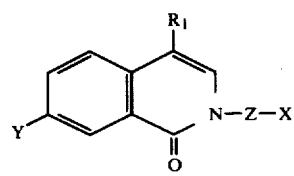

wherein Y, Z, $R_1$ and X are as defined above, and reacting the compound of the formula (VI) with an amine of the formula (VII)

wherein $R_2$ and $R_3$ are as defined above.

In the above alternative procedure, the reaction between the compounds of the formulae (II) and (IV) can be carried out using about 1 to about 1.5 mol of the hydroxyalkyl halide of the formula (IV) per mol of the compound of the formula (II) in an organic solvent such as dimethylformamide, toluene and the like, in the presence of a basic catalyst such as potassium carbonate, sodium carbonate, sodium hydride and the like in an amount of at least about 2 mols per mol of the compound of the formula (II), at a temperature of about 80° to about 140° C. for a period of about 1 to 5 hours.

The reaction of the thus obtained 2-(hydroxyalkyl)-1(2H)-isoquinolone compound of the formula (V) with a halogenating agent can be carried out by heating at reflux in the presence or absence of organic solvent for a period of about 30 minutes to about 2 hours. Suitable examples of halogenating agents are thionyl chloride, oxalyl chloride, phosphorus oxychloride, phosphorus oxybromide and the like. These halogenating agents may be used in a molar excess amount so as to serve as a solvent and in such case the organic solvent may not be used. Suitable examples of organic solvents are benzene, carbon tetrachloride, etc.

The subsequent reaction of the thus obtained 2-(haloalkyl)-1(2H)-isoquinolone of the formula (VI) with an amine of the formula (VII) can be conducted while heating at reflux for a period of about 1 to 6 hours, optionally in the presence of an inorganic basic catalyst as exemplified before the reaction of the compounds of the formulae (II) and (III). The reaction can be advantageously carried out using an organic solvent having a boiling point higher than that of the amine (VII) used, for example, xylene, tetralin, ethylbenzene, etc. When the amine used has a relatively low boiling point, the reaction is advantageously carried out in a sealed reaction vessel.

The compounds of the formula (I) having a substituted carbamoyl group at the 4-position can also be prepared by heat-reacting the 4-ester compound of the formula (I')

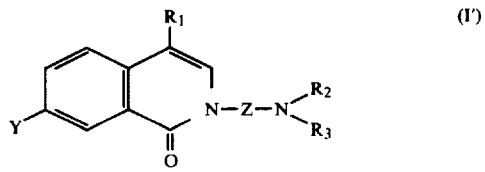

wherein $R_1$ is a lower alkoxycarbonyl group and Y, Z, $R_2$ and $R_3$ are as defined above, with an amine of the formula (VII) in an alcohol solvent.

Alternatively, the 4-carbamoyl compounds of the formula (I') above can be obtained by hydrolyzing the 2-(hydroxyalkyl)-1(2H)-isoquinolone compound of the formula (V)

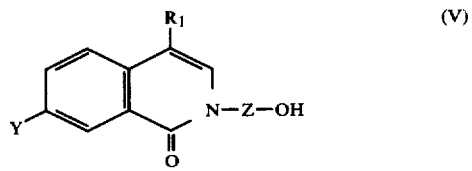

wherein $R_1$ represents a lower alkoxycarbonyl group, and Y and Z are as defined above, dissolved in an alkaline alcohol to obtain the corresponding 4-carboxy compound of the formula (VIII)

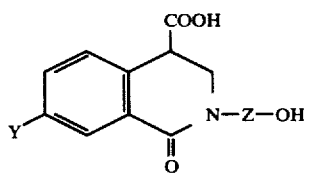

wherein Y and Z are as defined above, reacting the thus obtained 4-carboxy compound with a halogenating agent such as thionyl chloride, oxalyl chloride, phosphorus oxychloride, phosphorus oxybromide and the like in the presence of an organic solvent such as benzene or carbon tetrachloride, or in the absence of the organic solvent, for a period of about 1 to 3 hours to obtain the corresponding 4-acid halide compound of the formula (IX)

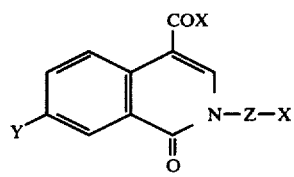

wherein X, Y and Z are as defined above, reacting the thus obtained 4-acid halide compound (IX) with an amine of the formula (VII) in an amount of at least about 2 mols per mol of the 4-acid halide compound (IX) in an organic solvent such as benzene, chloroform, diethyl ether at room temperature (about 15°–30° C.) for a period of about 1 to 5 hours to obtain the corresponding 4-carbamoyl compound of the formula (X)

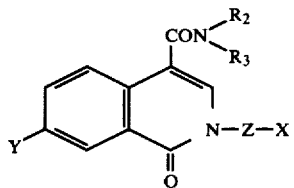

wherein X, Y, Z, $R_2$ and $R_3$ are as defined above, and reacting the resulting 4-carbamoyl compound of the formula (X) with an amine of the formula (VII) in an organic solvent such as acetone, benzene, toluene at a temperature of about 90° to about 150° C. for a period of about 1 to 6 hours to obtain the desired compound of the formula (I').

When the same amine is used in the amidation of the 4-acid halide compound (IX) and the amination of the 4-carbamoyl compound (X), these reactions are not necessary to conduct in two steps, and the desired compound of the formula (I') can be obtained in a single step by reacting the compound of the formula (IX) with an excess of the amine (VII) according to the procedure as described above for the reaction between the compounds of the formula (VI) or (X) and the amine (VII).

The object compounds of the formula (I) are generally obtained in the form of free base and, if desired, the free base can be easily converted into their acid addition salts by a conventional procedure well known in the art, for example, by reacting the free base with an inorganic or organic acid in a solvent such as ethanol, ethyl acetate, acetone and the like or an aqueous acid solution at room temperature or an elevated temperature.

The starting materials of the formula (II) wherein $R_1$ represents a cyano group or a lower alkoxycarbonyl group and Y represents chlorine or a methoxy group are novel compounds and can be obtained according to the following reaction scheme:

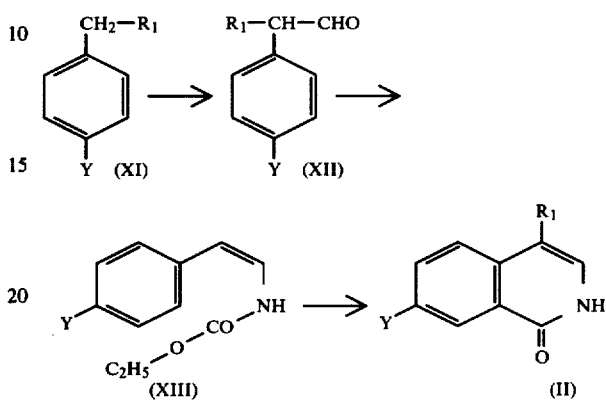

wherein Y is Cl or —OCH$_3$, and $R_1$ is —CN, —COOR (R=CH$_3$, C$_2$H$_5$, C$_3$H$_7$ or C$_4$H$_9$).

More specifically, 1 mol of a p-substituted phenylacetic acid lower alkyl ester of the formula (XI) (or an acetonitrile compound), about 1 to 1.5 mol of a sodium alkoxide and about 1.5 to 3 mols of ethyl formate are mixed in diethyl ether, and the mixture is allowed to react for about 10 to 24 hours at room temperature to obtain the formyl compound of the formula (XII). The resulting formyl compound and an equimolar amount of urethane are heat-refluxed in the presence of concentrated sulfuric acid in toluene to obtain the ethoxycarbonylamino compound of the formula (XIII) which is then heated under reflux in diphenyl ether to obtain the starting material of the formula (II).

The starting materials of the formula (II) having a lower alkoxycarbonyl group of 1 to 4 carbon atoms at the 4-position are novel compounds regardless of the type of substituent at the 7-position, and these compounds can be easily prepared by esterification of 4-carboxy compounds or transesterification of methoxy- or ethoxycarbonyl compounds. These reactions can be achieved using a desired alcohol in the presence of concentrated sulfuric acid while heating at reflux for about 10 to 20 hours.

The object compounds of the formula (I) thus obtained exhibit excellent analgesic, anti-reserpine (antidepressant), anti-histaminic, anticholinergic, gastric secretion inhibiting and anti-ulcer activities in mammals and, therefore, are useful as pharmaceutical agents.

The dose level of the compounds of the present invention as pharmaceutical agents varies depending upon the severity of conditions to be treated, the age of patients, the type of diseases or other factors, but generally ranges from 0.5 to 50 mg/kg of body weight per day in adult human administered as a single dose or multiple dose (divided into 2 to 3 doses).

The compounds of this invention can be administered orally, parenterally or intrarectally in various dosage forms such as tablets, capsules, granules, powders, injections, suppository, ointments and the like.

The above preparations are formulated as compositions comprising suitable carriers or excipients by the procedure generally used in preparing pharmaceutical compositions.

The tablets, capsules, granules, powders, etc. for oral administration can be prepared from excipients generally used in the art, for example, calcium carbonate, calcium phosphate, starch, sucrose, lactose, talc, magnesium stearate, geletin, polyvinylpyrrolidine, gum arabic, sorbitol, cystalline cellulose, polyethylene glycol, carboxymethylcellulose, silica and the like. Also, tablets and granules can be coated according to the method well known in the art.

The injections can be aqueous or oily suspensions, solutions, or powder filled in ampoules or freeze-dried preparation which is instantly dissolved in a liquid medium just before the use, and these preparations can be prepared according to the procedure well known in the art.

The suppositories can contain well-known carriers, for example, polyethylene glycol, lanolin, cacao butter, fatty acid triglycerides and the like.

The ointments can be prepared from conventional base materials by the procedure well known in the art.

The present invention is further illustrated in greater detail by the following Examples and Reference Examples, but they are not to be construed as limiting the present invention. Unless otherwise indicated, all parts, percents, ratios and the like are by weight.

EXAMPLE 1

22 g of 4-phenyl-1(2H)-isoquinolone and 30 g of anhydrous potassium carbonate were added to 100 ml of dimethylformamide and the mixture was stirred for 2 hours at 120° C. 18 g of 3-N,N-dimethylaminopropyl chloride was added to the solution and the mixture was stirred for 3 hours at 100° C. After completion of the reaction, the solvent was distilled off and water and subsequently dichloromethane were added to the residue, followed by thoroughly shaking. The dichloromethane layer was separated, washed with water and dried over anhydrous sodium sulfate. The solvent was distilled off and the residue was recrystallized from ligroin to obtain 23 g of 2-(3-N,N-dimethylaminopropyl)-4-phenyl-1(2H)-isoqunolone having a melting point of 95° C. as colorless prisms.

Elementary Analysis: Calcd for $C_{20}H_{22}N_2O = 306.411$: C, 78.40; H, 7.24; N, 9.14 (%). Found: C, 78.36; H, 7.32; N, 8.97 (%).

80 ml of a solution of 16 g of 2-(3-N,N-dimethylaminopropyl)-4-phenyl-1(2H)-isoquinolone in ethyl acetate and 100 ml of a solution of 8 g of tartaric acid in ethyl acetate were combined and the resulting mixture was warmed with stirring for a while. After allowing the mixture to cool, the precipitated crystals were filtered and recrystallized from a mixture of ethanol and petroleum ether to obtain 18 g of 2-(3-N,N-dimethylaminopropyl)-4-phenyl-1(2H)-isoquinolone tartrate having a melting point of 114° C. as colorless needles.

Elementary Analysis: Calcd for $C_{20}H_{22}N_2O \cdot C_4H_6O_6 = 456.500$: C, 63.15; H, 6.18; N, 6.14 (%). Found: C, 63.29; H, 6.23; N, 6.06 (%).

EXAMPLE 2

A mixture of 22.1 g of 4-phenyl-1(2H)-isoquinolone, 20 g of anhydrous potassium carbonate and 100 ml of dimethylformamide was stirred for 2 hours at 100° C. Then, 11 g of 3-chloropropanol was added to the resulting solution and the mixture was stirred at 110° C. for 5 hours. After completion of the reaction, the solvent was distilled off, and the residue was dissolved in dichloromethane. Water was added to the resulting solution and, after thoroughly stirring, the dichloromethane layer was separated and dried over anhydrous sodium sulfate. The solvent was distilled off, and the resulting residue was recrystallized from a mixture of ethyl acetate and petroleum ether to obtain 23 g of 2-(3-hydroxypropyl)-4-phenyl-1(2H)-isoquinolone having a melting point of 84° C. as colorless prisms.

Elementary Analysis: Calcd for $C_{18}H_{17}NO_2 = 279.342$: C, 77.40; H, 6.13; N, 5.01 (%). Found: C, 77.47; H, 6.09; N, 5.11 (%).

Then, 23 of 2-(3-hydroxypropyl)-4-phenyl-1-(2H)-isoquinolone was added to a mixture of 60 ml of benzene and 25 ml of thionyl chloride and the mixture was heated at reflux for 1 hour. The solvent was distilled off and the residue was dissolved in dichloromethane. The solution was washed with water and dried, and then the solvent was distilled off. The resulting crystals were recrystallized from a mixture of ethyl acetate and petroleum ether to obtain 23.3 g of 2-(3-chloropropyl)-4-phenyl-1(2H)-isoquinolone having a melting point of 138° C. as colorless prisms.

Elementary Analysis: Calcd for $C_{18}H_{16}ClNO = 297.787$: C, 72.60; H, 5.42; N, 4.70 (%). Found: C, 72.64; H, 5.40; N, 4.77 (%).

Then, 14.9 g of 2-(3-chloropropyl)-4-phenyl-1(2H)-isoquinolone, 7 g of anhydrous potassium carbonate and 40 ml of piperidine were mixed and heated at reflux for 5 hours. Thereafter, any excess of piperidine was distilled off and the residue was dissolved in dichloromethane. The solution was washed with water, dried and the solvent was distilled off. The resulting crystals were recrystallized from a mixture of diethyl ether and petroleum ether to obtain 15.6 g of 2-(3-piperidinopropyl)-4-phenyl-1(2H)-isoquinolone having a melting point of 117.5° C. as colorless prisms.

Elementary Analysis: Calcd for $C_{23}H_{26}N_2O = 346.476$: C, 79.73; H, 7.56; N, 8.09. Found: C, 79.85; H, 7.55; N, 8.00.

Then, 10.4 g of 2-(3-piperidinopropyl)-4-phenyl-1(2H)-isoquinolone was dissolved in 80 ml of ethyl acetate and 4 g of maleic acid was added to the solution, followed by stirring while warming. After cooling, the precipitated crystals were filtered and recrystallized from a mixture of diethyl ether and petroleum ether to obtain 12.2 g of 2-(3-piperidinopropyl)-4-phenyl-1(2H)-isoquinolone maleate having a melting point of 160.5° C. as colorless prisms.

Elementary Analysis: Calcd for $C_{23}H_{26}N_2O \cdot C_4H_4O_4 = 462.551$: C, 70.11; H, 6.54; N, 6.06 (%). Found: C, 70.05; H, 6.58; N, 6.02 (%).

The corresponding hydrobromic acid salt was obtained by the following procedure:

10.4 g of 2-(3-piperidinopropyl)-4-phenyl-1(2H)-isoquinolone was dissolved in 50 ml of acetone and 10 ml of a 47% aqueous solution of hydrobromic acid was added thereto and the mixture was warmed. After cooling, the precipitated crystals were filtered and recrystallized from a mixture of methanol and petroleum ether to obtain 11.6 g of 2-(3-piperidinopropyl)-4-phenyl-1(2H)-isoquinolone hydrobromide having a melting point of 300° C. as colorless needles.

Elementary Analysis: Calcd for $C_{23}H_{26}N_2O \cdot HBr = 427.393$: C, 64.64; H, 6.37; N, 6.55 (%). Found: C, 64.75; H, 6.37; N, 6.46 (%).

EXAMPLE 3

22 g of 7-chloro-4-ethoxycarbonyl-1(2H)-isoquinolone and 0.5 g of sodium hydride were added to 100 ml of toluene, and the mixture was heated at reflux. Thereafter, 20 g of N,N-dimethylaminopropyl chloride was added to the reaction mixture, followed by stirring for 2 hours at 100° C. The reaction mixture was then worked up in the same manner as described in Example 1 and the resulting crystals were recrystallized from petroleum ether to obtain 22.3 g of 7-chloro-2-(3-N,N-dimethylaminopropyl)-4-ethoxycarbonyl-1(2H)-isoquinolone having a melting point of 60° C. as colorless needles.

Elementary Analysis: Calcd for $C_{17}H_{21}ClN_2O_3 = 336.822$: C, 60.62; H, 6.28; N, 8.32 (%). Found: C, 60.55; H, 6.32; N, 8.21 (%).

Then, 7-chloro-2-(3-N,N-dimethylaminopropyl)-4-ethoxycarbonyl-1(2H)-isoquinolone was reacted with maleic acid in the same manner as described in Example 2 and the resulting crystals were recrystallized from a mixture of ethanol and petroleum ether to obtain 7-chloro-2-(3-N,N-dimethylaminopropyl)-4-ethoxycarbonyl-1(2H)-isoquinolone maleate.½ hydrate having a melting point of 146.5° C. as colorless needles.

Elementary Analysis: Calcd for $C_{17}H_{21}ClN_2O_3 \cdot C_4H_4O_4 \cdot \tfrac{1}{2}H_2O = 461.904$: C, 54.61; H, 5.67; N, 6.06 (%). Found: C, 54.78; H, 5.53; N, 5.95 (%).

EXAMPLE 4

25 g of 7-chloro-4-ethoxycarbonyl-1(2H)-isoquinolone was dissolved in 100 ml of dimethylformamide while warming, and 27 g of anhydrous potassium carbonate was added to the solution, followed by stirring for 2 hours at 110° C. Then, 14 g of 3-chloropropanol was added thereto and the stirring was continued for 5 hours at 110° C. The solvent was distilled off and the residue was dissolved in dichloromethane. The solution was washed with water, dried and the solvent was distilled off. The resulting crystals were recrystallized from a mixture of ethanol and petroleum ether to obtain 20.1 g of 7-chloro-4-ethoxycarbonyl-2-(3-hydroxypropyl)-1-(2H)-isoquinolone having a melting point of 193° C. as colorless prisms.

Elementary Analysis: Calcd for $C_{15}H_{16}ClNO_4 = 309.752$: C, 58.16; H, 5.21; N, 4.52 (%). Found: C, 58.29; H, 5.26; N, 4.53.

Then, 20.1 g of 7-chloro-4-ethoxycarbonyl-2-(3-hydroxypropyl)-1(2H)-isoquinolone was dissolved in 50 ml of ethanol, and 100 ml of an ethanolic solution of 5.5 g of potassium hydroxide was added to the resulting solution, followed by thoroughly stirring. The resulting solution was then poured into ice-water and the mixture was filtered. The filtrate was rendered neutral with dilute acetic acid and the precipitated crystals were filtered and washed with water. Recrystallization from a mixture of ethanol and petroleum ether gave 16.4 g of 4-carboxy-7-chloro-2-(3-hydroxypropyl)-1(2H)-isoquinolone having a melting point of 193° C. as colorless prisms.

Elementary Analysis: Calcd for $C_{13}H_{12}ClNO_4 = 281.698$: C, 55.43; H, 4.29; N, 4.97 (%). Found: C, 55.40; H, 4.38; N, 4.86 (%).

Then, 16.4 g of 4-carboxy-7-chloro-2-(3-hydroxypropyl)-1(2H)-isoquinolone was suspended in 100 ml of benzene, and 25 g of thionyl chloride was added to the suspension. The resulting mixture was heated at reflux for 3 hours and the solvent was distilled off. The residue was dissolved in dichloromethane and the solution was washed with water and dried. The solvent was distilled off and the resulting crystals were recrystallized from a mixture of ethyl acetate and petroleum ether to obtain 15.6 g of 7-chloro-4-chlorocarbonyl-2-(3-chloropropyl)-1(2H)-isoquinolone having a melting point of 125° C. as colorless prisms.

Elementary Analysis: Calcd for $C_{13}H_{10}Cl_3NO_2 = 318.589$: C, 49.01; H, 3.16; N, 4.40 (%). Found: C, 49.20; H, 3.10; N, 4.26 (%).

Then, a mixture of 3.2 g of 7-chloro-4-chlorocarbonyl-2-(3-chloropropyl)-1(2H)-isoquinolone, 100 ml of a 20% solution of dimethylamine in acetone and 2.5 g of anhydrous potassium carbonate was heated at 90°° C. in an autoclave for 6 hours. The solvent was distilled off and the residue was dissolved in dichloromethane. The solution was washed with water, dried and the solvent was distilled off. The resulting crystals were recrystallized from a mixture of ethanol and petroleum ether to obtain 2.5 g of 7-chloro-2-(3-N,N-dimethylaminopropyl)-4-N,N-dimethylcarbamoyl-1(2H)-isoquinolone having a melting point of 145° C. as colorless prisms.

Elementary Analysis: Calcd for $C_{17}H_{22}ClN_3O_2 = 335.837$: C, 60.80; H, 6.60; N, 12.51 (%). Found: C, 60;92; H, 6.63; N, 12.41 (%).

EXAMPLE 5

A mixture of 21.6 g of 4-ethoxycarbonyl-1(2H)-isoquinolone, 25 g of anhydrous potassium carbonate and 100 ml of dimethylformamide was heated at 100° C. for 2 hours. Then, 14 ml of 3-chloropropanol was added thereto and the mixture was heated at 110° C. for 4 hours. The solvent was distilled off and the residue was extracted with dichloromethane. The extract was washed with water, dried and the solvent was distilled off. 120 ml of an ethanolic solution of 5.5 g of potassium hydroxide was added to the residue, and the mixture was warmed. After cooling, the reaction mixture was poured into ice-water and then filtered. The filtrate was rendered neutral with dilute acetic acid, and the precipitated crystals were filtered and recrystallized from a mixture of ethanol and petroleum ether to obtain 12.5 g of 4-carboxy-2-(3-hydroxypropyl)-1(2H)-isoquinolone having a melting point of 205° C. as colorless prisms.

Elementary Analysis: Calcd for $C_{13}H_{13}NO_4 = 247.253$: C, 63.15; H, 5.30; N, 5.66 (%). Found: C, 63.23; H, 5.36; N, 5.54 (%).

Then, 12.5 g of 4-carboxy-2-(3-hydroxypropyl)-1(2H)-isoquinolone was added to a mixture of 50 ml of carbon tetrachloride and 25 ml of thionyl chloride, and the resulting mixture was heated at reflux for 2 hours. The solvent was distilled off and the residue was dissolved in dichloromethane. The solution was washed with water, dried and the solvent was distilled off. The resulting crystals were recrystallized from a mixture of ethyl acetate and petroleum ether to obtain 12.8 g of 4-chlorocarbonyl-2-(3-chloropropyl)-1(2H)-isoquinolone having a melting point of 101° C. as colorless prisms.

Elementary Analysis: Calcd for $C_{13}H_{11}Cl_2NO_2 = 284.144$: C, 54.95; H, 3.90; N, 4.93 (%). Found: C, 54.83; H, 3.92; N, 4.86 (%).

Then, 12.8 g of 4-chlorocarbonyl-2-(3-chloropropyl)-1-(2H)-isoquinolone was dissolved in 150 ml of chloroform, and a mixture of 6.6 g of n-butylamine and 20 ml of triethylamine was added thereto while stirring. After 5 hours, the reaction mixture was washed with water and dried. The solvent was distilled off and the resulting crystals were recrystallized from a mixture of ethyl acetate and petroleum ether to obtain 10 g of 4-N-n-butylcarbamoyl-2-(3-chloropropyl)-1(2H)-isoquinolone having a melting point of 149° C. as colorless prisms.

Elementary Analysis: Calcd for $C_{17}H_{21}ClN_2O_2 = 320.822$: C, 63.65; H, 6.60; N, 8.73 (%). Found: C, 63.79; H, 6.53; N, 8.70 (%).

Then, 10 g of 4-N-n-butylcarbamoyl-2-(3-chloropropyl)-1(2H)-isoquinolone, 9.5 g of anhydrous potassium carbonate and 200 ml of a 20% solution of dimethylamine in acetone were placed in an autoclave, and the mixture was heated at 90° C. for 5 hours. Thereafter, the reaction mixture was filtered and the solvent was distilled off from the filtrate. The resulting oily substance was reacted with oxalic acid in the same manner as described in Example 1 for the preparation of tartaric acid salt. The resulting crystals were recrystallized from a mixture of methanol and diethyl ether to obtain 7.5 g of 4-N-n-butylcarbamoyl-2-(3-N,N-dimethylaminopropyl)-1(2H)-isoquinolone oxalate having a melting point of 211° C. (with decomposition) as colorless prisms.

Elementary Analysis: Calcd for $C_{19}H_{27}N_3O_2.C_2H_2O_4 = 419.482$: C, 60.13; H, 6.97; N, 10.02 (%). Found: C, 60.29; H, 6.90; N, 10.08 (%).

The following compounds were prepared in the same manner as described in the foregoing Examples 1 to 5.

EXAMPLE 6

2-(2-N,N-Dimethylaminoethyl)-4-phenyl-1(2H)-isoquinolone. Recrystallized from a mixture of diethyl ether and petroleum ether. Colorless prisms having a melting point of 89° C.

Elementary Analysis: Calcd for $C_{19}H_{20}N_2O = 292.384$: C, 78.05; H, 6.89; N, 9.58 (%). Found: C, 78.09; H, 6.79; N, 9.63 (%).

2-(2-N,N-Dimethylaminoethyl)-4-phenyl-1(2H)-isoquinolone hydrochloride. Recrystallized from a mixture of ethanol and petroleum ether. Colorless needles having a melting point of 258.5° C.

Elementary Analysis: Calcd for $C_{19}H_{20}N_2O.HCl = 328.845$: C, 69.40; H, 6.44; N, 8.52 (%). Found: C, 69.48; H, 6.46; N, 8.53 (%).

EXAMPLE 7

2-(3-N,N-Diethylaminopropyl)-4-phenyl-1(2H)-isoquinolone. Recrystallized from petroleum ether. Colorless leaflets having a melting point of 41° C.

Elementary Analysis: Calcd for $C_{22}H_{26}N_2O = 334.465$: C, 79.01; H, 7.84; N, 8.38 (%). Found: C, 78.95; H, 7.91; N, 8.25 (%).

2-(3-N,N-Diethylaminopropyl)-4-phenyl-1(2H)-isoquinolone maleate. Recrystallized from a mixture of ethanol and diethyl ether. Colorless prisms having a melting point of 140° C.

Elementary Analysis: Calcd for $C_{22}H_{26}N_2O.C_4H_4O_4 = 450.539$: C, 69.31; H, 6.71; N, 6.22 (%). Found: C, 69.42; H, 6.73; N, 6.09 (%).

2-(3-N,N-Diethylaminopropyl)-4-phenyl-1(2H)-isoquinolone hydrobromide. Recrystallized from a mixture of methanol and petroleum ether. Colorless prisms having a melting point of 146.5° C.

Elementary Analysis: Calcd for $C_{22}H_{26}N_2O.HBr = 415.382$: C, 63.62; H, 6.55; N, 6.74 (%). Found: C, 63.75; H, 6.46; N, 6.69 (%).

EXAMPLE 8

4-Phenyl-2-(3-pyrrolidinopropyl)-1(2H)-isoquinolone. Recrystallized from diethyl ether and petroleum ether. Colorless prisms having a melting point of 115° C.

Elementary Analysis: Calcd for $C_{22}H_{24}N_2O = 332.449$: C, 79.48; H, 7.28; N, 8.43 (%). Found: C, 79.59; H, 7.33; N, 8.40 (%).

4-Phenyl-2-(3-pyrrolidinopropyl)-1(2H)-isoquinolone hydrobromide. Recrystallized from a mixture of methanol and petroleum ether. Colorless needles having a melting point of 277° C.

Elementary Analysis: Calcd for $C_{22}H_{24}N_2O.HBr = 413.366$: C, 63.93; H, 6.10; N, 6.78 (%). Found: C, 63.85; H, 6.16; N, 6.70 (%).

EXAMPLE 9

2-(3-Morpholinopropyl)-4-phenyl-1(2H)-isoquinolone. Recrystallized from a mixture of diethyl ether and petroleum ether. Colorless prisms having a melting point of 101° C.

Elementary Analysis: Calcd for $C_{22}H_{24}N_2O_2 = 348.449$: C, 75.83; H, 6.94; N, 8.04 (%). Found: C, 75.95; H, 6.99; N, 7.95 (%).

2-(3-Morpholinopropyl)-4-phenyl-1(2H)-isoquinolone maleate. Recrystallized from a mixture of ethanol and diethyl ether. Colorless leaflets having a melting point of 192° C.

Elementary Analysis: Calcd for $C_{22}H_{24}N_2O_2.C_4H_4O_4 = 464.523$: C, 67.23; H, 6.08; N, 6.03 (%). Found: C, 67.41; H, 6.15; N, 5.90 (%).

2-(3-Morpholinopropyl)-4-phenyl-1(2H)-isoquinolone hydrobromide. Recrystallized from a mixture of methanol and petroleum ether. Colorless needles having a melting point higher than 290° C.

Elementary Analysis: Calcd for $C_{22}H_{24}N_2O_2.HBr = 429.366$: C, 61.54; H, 5.87; N, 6.52 (%). Found: C, 61.63; H, 5.89; N, 6.44 (%).

EXAMPLE 10

2-{3-(4-Methylpiperazin-1-yl)propyl}-4-phenyl-1(2H)-isoquinolone. Recrystallized from a mixture of diethyl ether and petroleum ether. Colorless prisms having a melting point of 116° C.

Elementary Analysis: Calcd for $C_{23}H_{27}N_3O = 361.491$: C, 76.42; H, 7.53; N, 11.62 (%). Found: C, 76.49; H, 7.50; N, 11.63 (%).

EXAMPLE 11

2-[3-{4-(2-Hydroxyethyl)piperazin-1-yl}propyl]-4-phenyl-1(2H)-isoquinolone. Recrystallized from a mixture of ethyl acetate and petroleum ether. Colorless prisms having a melting point of 131° C.

Elementary Analysis: Calcd for $C_{24}H_{29}N_3O_2 = 391.518$: C, 73.63; H, 7.47; N, 10.73 (%). Found: C, 73.56; H, 7.49; N, 10.72 (%).

2-[3-{4-(2-Hydroxyethyl)piperazin-1-yl}propyl]-4-phenyl-1(2H)-isoquinolone dimaleate. Recrystallized from ethanol. Colorless prisms having a melting point of 192° C.

Elementary Analysis: Calcd for $C_{24}H_{29}N_3O_2.(C_4H_4O_4)_2 = 623.666$: C, 61.63; H, 5.98; N, 6.74 (%). Found: C, 61.83; H, 6.02; N, 6.63 (%).

EXAMPLE 12

2-(3-N-Isopropylaminopropyl)-4-phenyl-1(2H)-isoquinolone hydrobromide. Recrystallized from a mixture of ethanol and petroleum ether. Colorless needles having a melting point of 139° C.

Elementary Analysis: Calcd for $C_{21}H_{24}N_2O.HBr=401.355$: C, 62.85; H, 6.28; N, 6.98 (%). Found: C, 62.89; H, 6.35; N, 6.96 (%).

EXAMPLE 13

2-(2-N,N-Dimethylaminopropyl)-4-phenyl-1(2H)-isoquinolone. Recrystallized from a mixture of ethanol and n-hexane. Colorless flakes having a melting point of 107° C.

Elementary Analysis: Calcd for $C_{20}H_{22}N_2O=306.411$: C, 78.40; H, 7.24; N, 9.14 (%). Found: C, 78.51; H, 7.30; N, 9.00 (%).

2-(2-N,N-Dimethylaminopropyl)-4-phenyl-1(2H)-isoquinolone maleate. Recrystallized from a mixture of ethanol and diethyl ether. Colorless needles having a melting point of 139° C.

Elementary Analysis: Calcd for $C_{20}H_{22}N_2O.C_4H_4O_4=422.485$: C, 68.23; H, 6.20; N, 6.63 (%). Found: C, 68.35; H, 6.26; N, 6.69 (%).

EXAMPLE 14

2-(3-N,N-Dimethylamino-2-methylpropyl)-4-phenyl-1(2H)-isoquinolone maleate. Recrystallized from a mixture of methanol and diethyl ether. Colorless prisms having a melting point of 174° C.

Elementary Analysis: Calcd for $C_{21}H_{24}N_2O.C_4H_4O_4=436.512$: C, 68.79; H, 6.47; N, 6.42 (%). Found: C, 68.74; H, 6.56; N, 6.29 (%).

EXAMPLE 15

2-(3-N,N-Dimethylaminopropyl)-7-methoxy-4-(p-methoxyphenyl)-1(2H)-isoquinolone. Recrystallized from a mixture of diethyl ether and petroleum ether. Colorless needles having a melting point of 74° C.

Elementary Analysis: Calcd for $C_{22}H_{26}N_2O_3=366.464$: C, 72.11; H, 7.15; N, 7.64 (%). Found: C, 72.25; H, 7.15; N, 7.54 (%).

2-(3-N,N-Dimethylaminopropyl)-7-methoxy-4-(p-methoxyphenyl)-1(2H)-isoquinolone maleate. Recrystallized from a mixture of ethanol and diethyl ether. Colorless prisms having a melting point of 146° C.

Elementary Analysis: Calcd for $C_{22}H_{26}N_2O_3.C_4H_4O_4=482.538$: C, 64.72; H, 6.27; N, 5.81 (%). Found: C, 64.86; H, 6.15; N, 5.90 (%).

EXAMPLE 16

4-Cyano-2-(2-N,N-diethylaminoethyl)-1(2H)-isoquinolone. Recrystallized from ligroin. Colorless prisms having a melting point of 90° C.

Elementary Analysis: Calcd for $C_{16}H_{19}N_3O=269.349$: C, 71.35; H, 7.11; N, 15.60 (%). Found: C, 71.29; H, 7.16; N, 15.52 (%).

4-Cyano-2-(2-N,N-diethylaminoethyl)-1(2H)-isoquinolone maleate. Recrystallized from a mixture of ethanol and diethyl ether. Colorless needles having a melting point of 145° C.

Elementary Analysis: Calcd for $C_{16}H_{19}N_3O.C_4H_4O_4=385.423$: C, 62.33; H, 6.02; N, 10.90 (%). Found: C, 62.20; H, 5.89; N, 10.85 (%).

EXAMPLE 17

4-Cyano-2-(3-N,N-dimethylaminopropyl)-1(2H)-isoquinolone monohydrate. Recrystallized from petroleum ether. Colorless needles having a melting point of 60° C.

Elementary Analysis: Calcd for $C_{15}H_{17}N_3O.H_2O=273.338$: C, 65.91; H, 7.01; N, 15.37 (%). Found: C, 65.84; H, 6.85; N, 15.35 (%).

4-Cyano-2-(3-N,N-dimethylaminopropyl)-1(2H)-isoquinolone tartrate hemihydrate. Recrystallized from a mixture of methanol and petroleum ether. Colorless prisms having a melting point of 178° C.

Elementary Analysis: Calcd for $C_{15}H_{17}N_3O.C_4H_6O_6.1/2H_2O=414.416$: C, 55.07; H, 5.83; N, 10.14 (%). Found: C, 55.16; H, 5.66; N, 9.97 (%).

EXAMPLE 18

4-Cyano-2-(3-N,N-dimethylaminopropyl)-7-methoxy-1(2H)-isoquinolone. Recrystallized from ligroin. Colorless prisms having a melting point of 116° C.

Elementary Analysis: Calcd for $C_{16}H_{19}N_3O_2=285.349$: C, 67.35; H, 6.71; N, 14.73 (%). Found: C, 67.43; H, 6.75; N, 14.60 (%).

4-Cyano-2-(3-N,N-dimethylaminopropyl)-7-methoxy-1(2H)-isoquinolone maleate. Recrystallized from a mixture of ethanol and diethyl ether. Colorless prisms having a melting point of 174° C.

Elementary Analysis: Calcd for $C_{16}H_{19}N_3O_2.C_4H_4O_4=401.423$; C, 59.84; H, 5.78; N, 10.47 (%). Found: C, 59.73; H, 5.76; N, 10.55 (%).

EXAMPLE 19

2-(3-N,N-dimethylaminopropyl)-4-ethoxycarbonyl-1(2H)-isoquinolone tartrate hemihydrate. Recrystallized from a mixture of ethanol and diethyl ether. Colorless needles having a melting point of 184° C. (with decomposition).

Elementary Analysis: Calcd for $C_{17}H_{22}N_2O_3.C_4H_6O_6.1/2H_2O=463.473$: C, 54.42; H, 6.31; N, 6.04 (%). Found: C, 54.60; H, 6.25; N, 6.23 (%).

EXAMPLE 20

2-(3-N,N-Dimethylaminopropyl)-4-ethoxycarbonyl-7-methoxy-1(2H)-isoquinolone. Recrystallized from petroleum ether. Colorless needles having a melting point of 50° C.

Elementary Analysis: Calcd for $C_{18}H_{24}N_2O_4=332.403$: C, 65.04; H, 7.28; N, 8.43 (%). Found: C, 65.10; H, 7.22; N, 8.43 (%).

2-(3-N,N-dimethylaminopropyl)-4-ethoxycarbonyl-7-methoxy-1(2H)-isoquinolone maleate hemihydrate. Recrystallized from a mixture of ethanol and diethyl ether. Colorless leaflets having a melting point of 121° C.

Elementary Analysis: Calcd for $C_{18}H_{24}N_2O_4.C_4H_4O_4.1/2H_2O$: C, 57.76; H, 6.39; N, 6.12 (%). Found: C, 57.73; H, 6.21; N, 6.19 (%).

EXAMPLE 21

7-Chloro-4-(p-chlorophenyl)-2-(3-N,N-dimethylaminopropyl)-1(2H)-isoquinolone. Recrystallized from ligroin. Colorless prisms having a melting point of 100° C.

Elementary Analysis: Calcd for $C_{20}H_{20}Cl_2N_2O=375.301$: C, 64.01; H, 5.37; N, 7.46 (%). Found: C, 64.20; H, 5.31; N, 7.47 (%).

7-Chloro-4-(p-chlorophenyl)-2-(3-N,N-dimethylaminopropyl)-1(2H)-isoquinolone tartrate. Recrystallized from a mixture of ethanol and diethyl ether. Colorless crystalline powder having a melting point of 192° C.

Elementary Analysis: Calcd for $C_{20}H_{20}Cl_2N_2O.C_4H_6O_6=525.390$: C, 54.87; H, 4.99; N, 5.33 (%). Found: C, 54.97; H, 4.96; N, 5.46 (%).

EXAMPLE 22

7-Chloro-2-(3-N,N-dimethylaminopropyl)-4-N,N-dimethylcarbamoyl-1(2H)-isoquinolone oxalate. Recrystallized from a mixture of ethanol and diethyl ether. Colorless needles having a melting point of 223° C.

Elementary Analysis: Calcd for $C_{17}H_{22}ClN_3O_2.C_2H_2O_4=425.873$: C, 53.59; H, 5.68; N, 9.87 (%). Found: C, 53.46; H, 5.62; N, 9.88 (%).

EXAMPLE 23

7-Chloro-4-(4-methylpiperazin-1-yl-carbonyl)-2-{3-(4-methylpiperazin-1-yl)propyl}-1(2H)-isoquinolone. Recrystallized from a mixture of diethyl ether and petroleum ether. Colorless prisms having a melting point of 128° C.

Elementary Analysis: Calcd for $C_{23}H_{32}ClN_5O_2=445.997$: C, 61.94; H, 7.23; N, 15.70 (%). Found: C, 62.06; H, 7.36; N, 15.61 (%).

7-Chloro-4-(4-methylpiperazin-1-yl-carbonyl)-2-{3-(4-methylpiperazin-1-yl)propyl}-1(2H)-isoquinolone tri-maleate. Recrystallized from a mixture of methanol and diethyl ether. Colorless crystalline powder having a melting point of 146° C.

Elementary Analysis: Calcd for $C_{23}H_{32}ClN_5O_2.3C_4H_4O_4=794.219$: C, 52.93; H, 5.58; N, 8.82 (%). Found: C, 52.86; H, 5.66; N, 8.70 (%).

EXAMPLE 24

7-Chloro-4-morpholinocarbonyl-2-(3-morpholinopropyl)-1(2H)-isoquinolone. Recrystallized from a mixture of ethyl acetate and petroleum ether. Colorless prisms having a melting point of 178° C.

Elementary Analysis: Calcd for $C_{21}H_{26}ClN_3O_4=419.912$: C, 60.07; H, 6.24; N, 10.01 (%). Found: C, 60.16; H, 6.22; N, 9.83 (%).

7-Chloro-4-morpholinocarbonyl-2-(3-morpholinopropyl)-1(2H)-isoquinolone maleate. Recrystallized from a mixture of ethanol and diethyl ether. Colorless needles having a melting point of 178° C.

Elementary Analysis: Calcd for $C_{21}H_{26}ClN_3O_4.C_4H_4O_4=535.986$: C, 56.02; H, 5.64; N, 7.84 (%). Found: C, 56.16; H, 5.70; N, 7.88 (%).

EXAMPLE 25

4-Carbamoyl-2-(3-N,N-dimethylaminopropyl)-1(2H)-isoquinolone monohydrate. Recrystallized from a mixture of ethanol and petroleum ether. Colorless crystalline powder having a melting point of 159° C. (with decomposition).

Elementary Analysis: Calcd for $C_{15}H_{19}N_3O_2.H_2O=291.353$: C, 61.84; H, 7.27; N, 14.42 (%). Found: C, 61.79; H, 7.30; N, 14.55 (%).

4-Carbamoyl-2-(3-N,N-dimethylaminopropyl)-1(2H)-isoquinolone oxalate. Recrystallized from a mixture of ethanol and petroleum ether. Colorless crystalline powder having a melting point of 156° C.

Elementary Analysis: Calcd for $C_{15}H_{19}N_3O_2.C_2H_2O_4=363.373$: C, 56.19; H, 5.83; N, 11.56 (%). Found: C, 56.32; H, 5.72; N, 11.46 (%).

EXAMPLE 26

2-(3-N,N-Diethylaminopropyl)-4-N,N-diethylcarbamoyl-1(2H)-isoquinolone oxalate. Recrystallized from a mixture of methanol and diethyl ether. Colorless prisms having a melting point of 168° C.

Elementary Analysis: Calcd for $C_{21}H_{31}N_3O_2.C_2H_2O_4=447.536$: C, 61.73; H, 7.43; N, 9.39 (%). Found: C, 61.65; H, 7.49; N, 9.30 (%).

EXAMPLE 27

4-n-Butoxycarbonyl-2-(3-N,N-dimethylaminopropyl)-1(2H)-isoquinolone maleate. Recrystallized from a mixture of ethanol and diethyl ether. Colorless prisms having a melting point of 142° C.

Elementary Analysis: Calcd for $C_{19}H_{26}N_2O_3.C_4H_4O_4=446.505$: C, 61.87; H, 6.77; N, 6.27 (%). Found: C, 61.99; H, 6.76; N, 6.24 (%).

EXAMPLE 28

2-(2-N,N-Diethylaminoethyl)-4-phenyl-1(2H)-isoquinolone maleate. Recrystallized from a mixture of ethanol and diethyl ether. Colorless needles having a melting point of 197.5° C.

Elementary Analysis: Calcd for $C_{21}H_{24}N_2O.C_4H_4O_4=436.512$: C, 68.79; H, 6.47; N, 6.42 (%). Found: C, 68.93; H, 6.55; N, 6.39 (%).

EXAMPLE 29

4-Phenyl-2-(2-pyrrolidinoethyl)-1(2H)-isoquinolone. Recrystallized from a mixture of ethyl acetate and petroleum ether. Colorless prisms having a melting point of 131.5° C.

Elementary Analysis: Calcd for $C_{21}H_{22}N_2O=318.422$: C, 79.21; H, 6.96; N, 8.80 (%). Found: C, 79.16; H, 7.04; N, 8.69 (%).

4-Phenyl-2-(2-pyrrolidinoethyl)-1(2H)-isoquinolone maleate. Recrystallized from a mixture of ethanol and diethyl ether. Colorless needles having a melting point of 176.5° C.

Elementary Analysis: Calcd for $C_{21}H_{22}N_2O.C_4H_4O_4=434.496$: C, 69.11; H, 6.03; N, 6.45 (%). Found: C, 69.29; H, 5.91; N, 6.55 (%).

EXAMPLE 30

2-(2-N,N-Diethylaminopropyl)-4-phenyl-1(2H)-isoquinolone. Recrystallized from a mixture of diethyl ether and petroleum ether. Colorless prisms having a melting point of 92° C.

Elementary Analysis: Calcd for $C_{22}H_{26}N_2O=334.465$: C, 79.01; H, 7.84; N, 8.38 (%). Found: C, 79.00; H, 7.69; N, 8.45 (%).

2-(2-N,N-Diethylaminopropyl)-4-phenyl-1(2H)-isoquinolone hydrochloride. Recrystallized from a mixture of methanol and diethyl ether. Colorless needles having a melting point of 203° C.

Elementary Analysis: Calcd for $C_{22}H_{26}N_2O.HCl=370.926$: C, 71.24; H, 7.34; N, 7.55 (%). Found: C, 71.32; H, 7.31; N, 7.38 (%).

2-(2-N,N-Diethylaminopropyl)-4-phenyl-1(2H)-isoquinolone maleate. Recrystallized from a mixture of methanol and diethyl ether. Colorless prisms having a melting point of 142° C.

Elementary Analysis: Calcd for $C_{22}H_{26}N_2O.C_4H_4O_4=450.539$: C, 69.31; H, 6.71; N, 6.22 (%). Found: C, 69.51; H, 6.78; N, 6.25 (%).

EXAMPLE 31

2-{2-(4-methylpiperazin-1-yl)ethyl}-4-phenyl-1(2H)-isoquinolone. Recrystallized from a mixture of ethyl acetate and petroleum ether. Colorless prisms having a melting point of 103.5° C.

Elementary Analysis: Calcd for $C_{22}H_{25}N_3O = 347.464$: C, 76.05; H, 7.25; N, 12.09 (%). Found: C, 75.92; H, 7.31; N, 11.95 (%).

2-{2-(4-methylpiperazin-1-yl)ethyl}-4-phenyl-1(2H)-isoquinolone dimaleate. Recrystallized from a mixture of dimethylformamide and methanol. White crystalline powder having a melting point of 207° C. (with decomposition).

Elementary Analysis: Calcd for $C_{22}H_{25}N_3O.2C_4H_4O_4 = 579.612$: C, 62.17; H, 5.74; N, 7.25 (%). Found: C, 62.30; H, 5.65; N, 7.10 (%).

EXAMPLE 32

4-Phenyl-2-(2-pyrrolidinopropyl)-1(2H)-isoquinolone. Recrystallized from a mixture of diethyl ether and petroleum ether. Colorless prisms having a melting point of 84° C.

Elementary Analysis: Calcd for $C_{22}H_{24}N_2O = 332.449$: C, 79.48; H, 7.28; N, 8.43 (%). Found: C, 79.44; H, 7.25; N, 8.41 (%).

4-Phenyl-2-(2-pyrrolidinopropyl)-1(2H)-isoquinolone hydrochloride. Recrystallized from a mixture of ethanol and diethyl ether. Colorless needles having a melting point of 237° C. (with decomposition).

Elementary Analysis: Calcd for $C_{22}H_{24}N_2O.HCl = 368.910$: C, 71.63; H, 6.83; N, 7.59 (%). Found: C, 71.56; H, 6.90; N, 7.66 (%).

EXAMPLE 33

4-Phenyl-2-(2-piperizinopropyl)-1(2H)-isoquinolone hydrochloride. Recrystallized from a mixture of ethanol and diethyl ether. White crystalline powder having a melting point of 250° C. (with decomposition).

Elementary Analysis: Calcd for $C_{23}H_{26}N_2O.HCl = B$ 382.937: C, 72.14; H, 7.11; N, 7.32 (%). Found: C, 72.26; H, 7.13; N, 7.20 (%).

EXAMPLE 34

2-{2-(4-Methylpiperazin-1-yl)propyl}-4-phenyl-1(2H)-isoquinolone dimaleate. Recrystallized from a mixture of dimethylformamide and ethanol. White crystalline powder having a melting point of 189.5° C.

Elementary Analysis: Calcd for $C_{23}H_{27}N_3O.2C_4H_4O_4 = 593.639$: C, 62.72; H, 5.94; N, 7.08 (%). Found: C, 62.93; H, 5.81; N, 7.15 (%).

EXAMPLE 35

7-Chloro-4-(p-chlorophenyl)-2-(2-N,N-diethylaminoethyl)-1(2H)-isoquinolone. Recrystallized from petroleum ether. Colorless prisms having a melting point of 90° C.

Elementary Analysis: Calcd for $C_{21}H_{22}Cl_2N_2O = 389.328$: C, 64.79; H, 5.70; N, 7.20 (%). Found: C, 64.71; H, 5.73; N, 7.14 (%).

7-Chloro-4-(p-chlorophenyl)-2-(2-N,N-diethylaminoethyl)-1(2H)-isoquinolone maleate. Recrystallized from a mixture of ethanol and diethyl ether. Colorless prisms having a melting point of 134° C.

Elementary Analysis: Calcd for $C_{21}H_{22}Cl_2N_2O.C_4H_4O_4 = 505.402$: C, 59.41; H, 5.19; N, 5.54 (%). Found: C, 59.27; H, 5.25; N, 5.63 (%).

EXAMPLE 36

7-Chloro-4-(p-chlorophenyl)-2-(2-N,N-diethylaminopropyl)-1(2H)-isoquinolone. Recrystallized from petroleum ether. Colorless prisms having a melting point of 107° C.

Elementary Analysis: Calcd for $C_{22}H_{24}Cl_2N_2O = 403.355$: C, 65.51; H, 6.00; N, 6.95 (%). Found: C, 65.68; H, 6.11; N, 6.87 (%).

7-Chloro-4-(p-chlorophenyl)-2-(2-N,N-diethylaminopropyl)-1(2H)-isoquinolone hydrochloride. Recrystallized from aqueous ethanol. Colorless prisms having a melting point of 195° C.

Elementary Analysis: Calcd for $C_{22}H_{24}Cl_2N_2O.HCl = 439.816$: C, 60.08; H, 5.73; N, 6.37 (%). Found: C, 60.18; H, 5.62; N, 6.49 (%).

7-Chloro-4-(p-chlorophenyl)-2-(2-N,N-diethylaminopropyl)-1(2H)-isoquinolone maleate. Recrystallized from a mixture of ethanol and diethyl ether. White crystalline powder having a melting point of 112° C.

Elementary Analysis: Calcd for $C_{22}H_{24}Cl_2N_2O.C_4H_4O_4 = 519.429$. C, 60.12; H, 5.43; N, 5.39 (%). Found: C, 60.06; H, 5.55; N, 5.26 (%).

EXAMPLE 37

2-(2-N,N-Diethylaminoethyl)-7-methoxy-4-(p-methoxyphenyl)-1(2H)-isoquinolone maleate. Recrystallized from a mixture of methanol and diethyl ether. Colorless prisms having a melting point of 161° C.

Elementary Analysis: Calcd for $C_{23}H_{28}N_2O_3.C_4H_4O_4 = 496.565$: C, 65.31; H, 6.50; N, 5.64 (%). Found: C, 65.48; H, 6.48; N, 5.53 (%).

EXAMPLE 38

2-(2-N,N-Diethylaminoethyl)-4-ethoxycarbonyl-7-methoxy-1(2H)-isoquinolone. Recrystallized from petroleum ether. Colorless prisms having a melting point of 47° C.

Elementary Analysis: Calcd for $C_{19}H_{26}N_2O_4 = 346.430$: C, 65.88; H, 7.56; N, 8.09 (%). Found: C, 65.81; H, 7.62; N, 8.06 (%).

2-(2-N,N-Diethylaminoethyl)-4-ethoxycarbonyl-7-methoxy-1(2H)-isoquinolone maleate. Recrystallized from a mixture of ethanol and diethyl ether. Colorless needles having a melting point of 135° C.

Elementary Analysis: Calcd for $C_{19}H_{26}N_2O_4.C_4H_4O_4 = 462.504$: C, 59.73; H, 6.54; N, 6.06 (%). Found: C, 59.90; H, 6.50; N, 6.14 (%).

EXAMPLE 39

2-(2-N,N-Diethylaminopropyl)-7-methoxy-4-(p-methoxyphenyl)-1(2H)-isoquinolone hydrochloride. Recrystallized from a mixture of ethanol and diethyl ether. Colorless prisms having a melting point of 244° C.

Elementary Analysis: Calcd for $C_{24}H_{30}N_2O_3.HCl = 430.979$: C, 66.89; H, 7.25; N, 6.50 (%). Found: C, 66.76; H, 7.28; N, 6.48 (%).

EXAMPLE 40

2-(2-N,N-Diethylaminopropyl)-4-ethoxycarbonyl-7-methoxy-1(2H)-isoquinolone. Recrystallized from petroleum ether. Colorless prisms having a melting point of 100° C.

Elementary Analysis: Calcd for $C_{20}H_{28}N_2O_4 = 360.457$: C, 66.64; H, 7.83; N, 7.77 (%). Found: C, 66.78; H, 7.70; N, 7.65 (%).

EXAMPLE 41

2-(2-N,N-Diethylamino-1-methylethyl)-4-phenyl-1(2H)-isoquinolone. Recrystallized from a mixture of diethyl ether and petroleum ether. Colorless prisms having a melting point of 95° C.

Elementary Analysis: Calcd for $C_{22}H_{26}N_2O = 334.465$: C, 79.01; H, 7.84; N, 8.38 (%). Found: C, 79.10; H, 7.90; N, 8.25 (%).

2-(2-N,N-Diethylamino-1-methylethyl)-4-phenyl-1(2H)-isoquinolone hydrochloride. Recrystallized from a mixture of ethanol and diethyl ether. Colorless prisms having a melting point of 198° C. (with decomposition).

Elementary Analysis: Calcd for $C_{22}H_{26}N_2O\cdot HCl = 370.926$: C, 71.24; H, 7.34; N, 7.55 (%). Found: C, 71.16; H, 7.45; N, 7.60 (%).

EXAMPLE 42

4-Cyano-2-(2-N,N-diethylaminopropyl)-1(2H)-isoquinolone. Recrystallized from a mixture of diethyl ether and petroleum ether. Colorless prisms having a melting point of 93° C.

Elementary Analysis: Calcd for $C_{17}H_{21}N_3O = 283.376$: C, 72.06; H, 7.47; N, 14.83 (%). Found: C, 71.91; H, 7.55; N, 14.79 (%).

4-Cyano-2-(2-N,N-diethylaminopropyl)-1(2H)-isoquinolone maleate. Recrystallized from a mixture of methanol and diethyl ether. Colorless prisms having a melting point of 148° C.

Elementary Analysis: Calcd for $C_{17}H_{21}N_3O\cdot C_4H_4O_4 = 399.451$: C, 63.15; H, 6.31; N, 10.52 (%). Found: C, 63.31; H, 6.22; N, 10.44.

EXAMPLE 43

4-Cyano-2-(2-N,N-dimethylaminopropyl)-1(2H)-isoquinolone. Recrystallized from a mixture of ethyl acetate and petroleum ether. Colorless prisms having a melting point of 141° C.

Elementary Analysis: Calcd for $C_{15}H_{17}N_3O = 255.322$: C, 70.56; H, 6.71; N, 16.46 (%). Found: C, 70.44; H, 6.71; N, 16.59 (%).

4-Cyano-2-(2-N,N-dimethylaminopropyl)-1(2H)-isoquinolone maleate. Recrystallized from a mixture of methanol and diethyl ether. White crystalline powder having a melting point of 177° C.

Elementary Analysis: Calcd for $C_{15}H_{17}N_3O\cdot C_4H_4O_4 = 371.396$: C, 61.45; H, 5.70; N, 11.31 (%). Found: C, 61.61; H, 5.78; N, 11.33 (%).

EXAMPLE 44

2-(2-N,N-Diethylaminopropyl)-4-phenyl-7-methoxy-1(2H)-isoquinolone maleate. Recrystallized from a mixture of ethyl acetate and diethyl ether. Colorless needles having a melting point of 98° C.

Elementary Analysis: Calcd for $C_{23}H_{28}N_2O_2\cdot C_4H_4O_4 = 480.560$ C, 67.48; H, 6.71; N, 5.83 (%). Found: C, 67.31; H, 6.66; N, 5.88 (%).

EXAMPLE 45

4-(p-Methoxyphenyl)-2-(2-N,N-diethylaminoethyl)-1(2H)-isoquinolone hydrochloride hemihydrate. Recrystallized from a mixture of ethanol and diethyl ether. White needles having a melting point of 193° C.

Elementary Analysis: Calcd for $C_{22}H_{26}N_2O_2\cdot HCl\cdot \frac{1}{2}H_2O = 395.933$: C, 66.74; H, 7.13; N, 7.07 (%). Found: C, 66.74; H, 6.91; N, 7.18 (%).

EXAMPLE 46

4-(p-Chlorophenyl)-2-(2-N,N-diethylaminoethyl)-1(2H)-isoquinolone hydrochloride hemihydrate. Recrystallized from a mixture of methanol and diethyl ether. White crystalline powder having a melting point of 194° C.

Elementary Analysis: Calcd for $C_{21}H_{23}ClN_2O\cdot HCl\cdot \frac{1}{2}H_2O = 400.343$: C, 63.00; H, 6.29; N, 7.00 (%). Found C, 62.97; H, 6.17 N, 7.30 (%).

The pharmacological activities, acute toxicity and pharmaceutical preparations of typical examples of the compounds of this invention having the formula (I) are illustrated below, in comparison with the typical known compounds.

Compounds of Present Invention

Compound A: 2-(3-N,N-dimethylaminopropyl)-4-phenyl-1(2H)-isoquinolone tartrate (prepared in Example 1).

Compound B: 2-(2-N,N-dimethylaminoethyl)-4-phenyl-1(2H)-isoquinolone hydrochloride (prepared in Example 6).

Compound C: 4-cyano-2-(3-N,N-dimethylaminopropyl)-1(2H)-isoquinolone tartrate ¼ hydrate (prepared in Example 17).

Compound D: 2-(2-N,N-dimethylaminopropyl)-4-phenyl-1(2H)-isoquinolone maleate (prepared in Example 13).

Analgesic Activity

According to the acetic acid stretching method described by Koster et al [Fed. Pro., 18, 412 (1959)], Compound A was administered orally to ddy male mice (body weight, 20 to 25 g) fasted overnight before test. One hour after administration of Compound A, a 0.6% aqueous acetic acid solution was administered intraperitoneally at a dose of 0.35 ml per mouse and the stretching of the mice was observed 10 minutes after the administration of the acetic acid solution for a period of 10 minutes, and the percent inhibition was calculated.

The results obtained are shown in Table 1 below. These results clearly indicate that Compound A inhibited the pain reaction induced by acetic acid injection, at the dose of 50 and 100 mg/kg of Compound A, depending on the dose level.

TABLE 1

| Compound | Analgesic Activity | | | |
|---|---|---|---|---|
| | Dose (mg/kg) | Number of Animals | Number of Stretching | Percent Inhibition (%) |
| Control | | 8 | 36.5 ± 6.5 | |
| Compound A | 25 | 8 | 33.8 ± 8.2 | — |
| Compound A | 50 | 8 | 16.9 ± 4.8* | 53.7 |
| Compound A | 100 | 8 | 10.0 ± 2.8** | 72.6 |

*$p < 0.05$
**$p < 0.01$

Anti-Reserpine Activity (Anti-Depression Activity)

Reserpine was administered subcutaneously to ddy male mice (body weight, 25 to 30 g) at a dose of 2 mg/kg and, after fasting for 18 hours, reserpine was again administered subcutaneously at a dose of 2 mg/kg. Five hours after the second administration of reserpine, the mice which indicated a constant decrease in body temperature were selected and administered orally with the test compound (Compound C), followed by measuring the rectal temperature of the mice at one hour intervals.

Figure 1A:
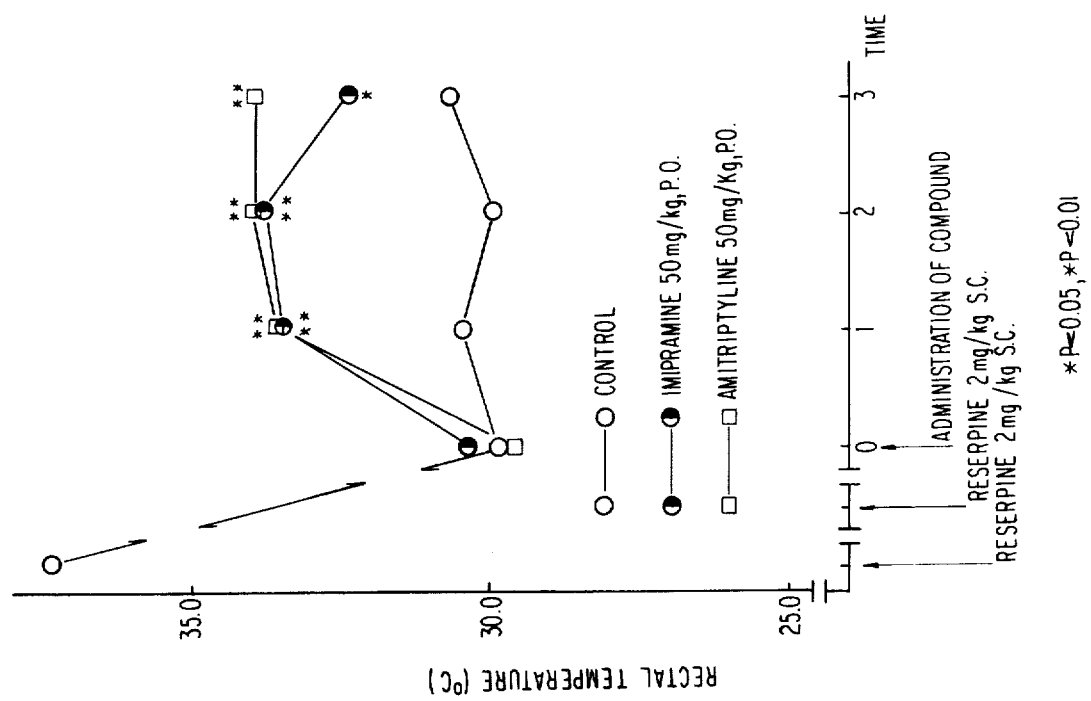

The results obtained are shown in FIG. 1(a) and FIG. 1(b). These results indicate that Compound C increases at a dose of 50 and 100 mg/kg significantly the rectal temperature which has been decreased by the pretreatment with reserpine.

In this experiment, Imipramine (10,11-dihydro-N,N-dimethyl-5H-dibenz[b,f]azepine-5-propanamine) and Amitriptyline [3-(10,11-dihydro-5H-dibenzo[a,d]-cyclohepten-5-ylidene)-N,N-dimethyl-1-propanamine] were used as typical examples of known compounds for comparison and the results obtained with these compounds are also shown in FIG. 1(a).

Anti-histamine and Anti-cholinergic Activities

The ileum of guinea pig (body weight, 300 to 400 g) was extracted and suspended in a Magnus tobe containing Tyrode's solution (saturated with oxygen) at 31° C. and the inhibitory activity of the test compounds on the contraction induced by administration of histamine or acetylchloline was determined. The treatment with the test compounds was conducted 30 seconds before inducing the contraction.

Figure 2B:
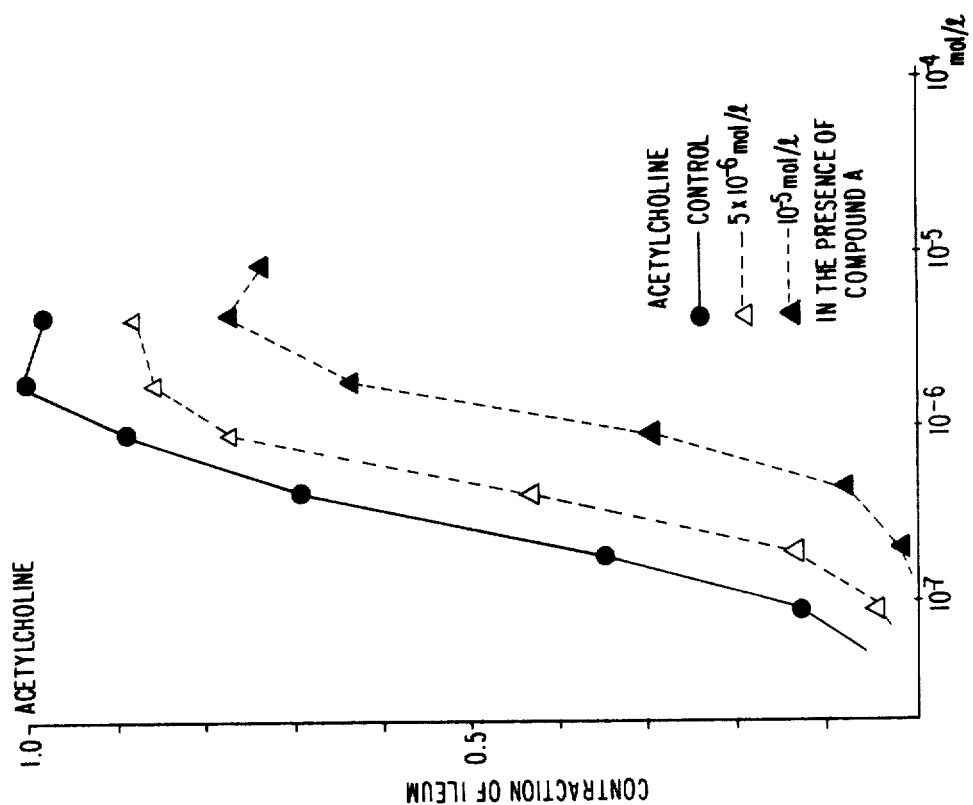
FIGS. 2(a) and 2(b) are graphs showing the anti-histamine activity and the anti-cholinergic activity of Compound A of this invention.
Figure 2A:
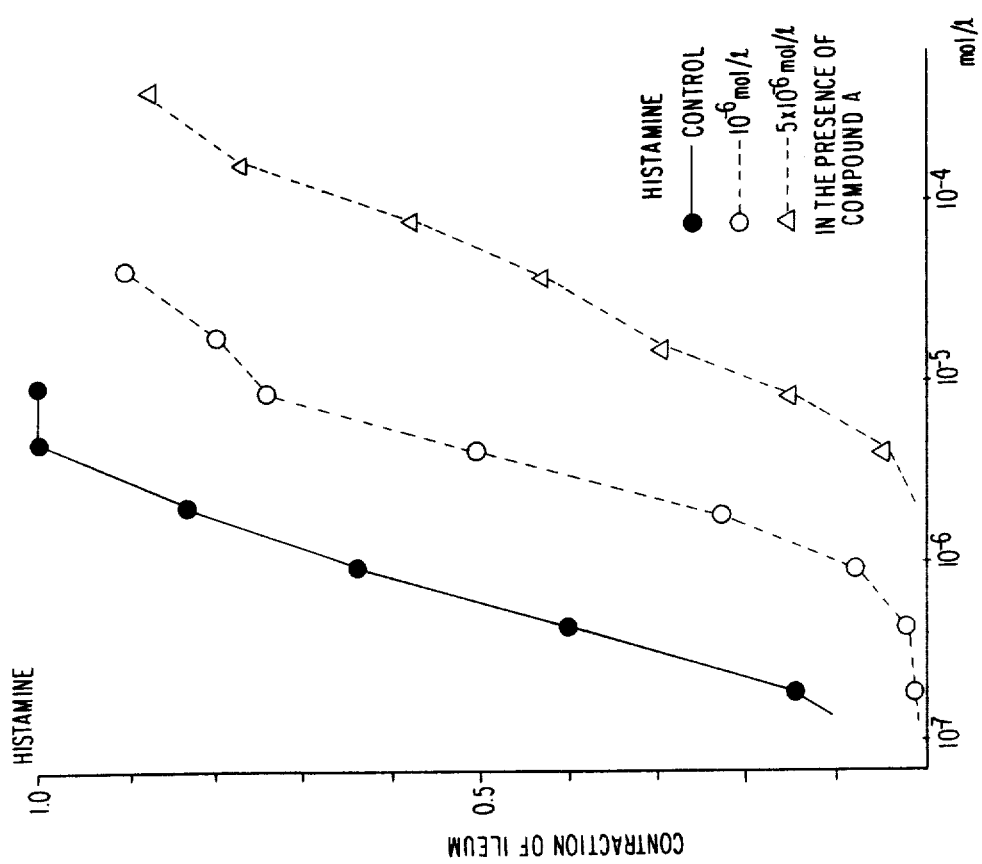
Figure 3B:
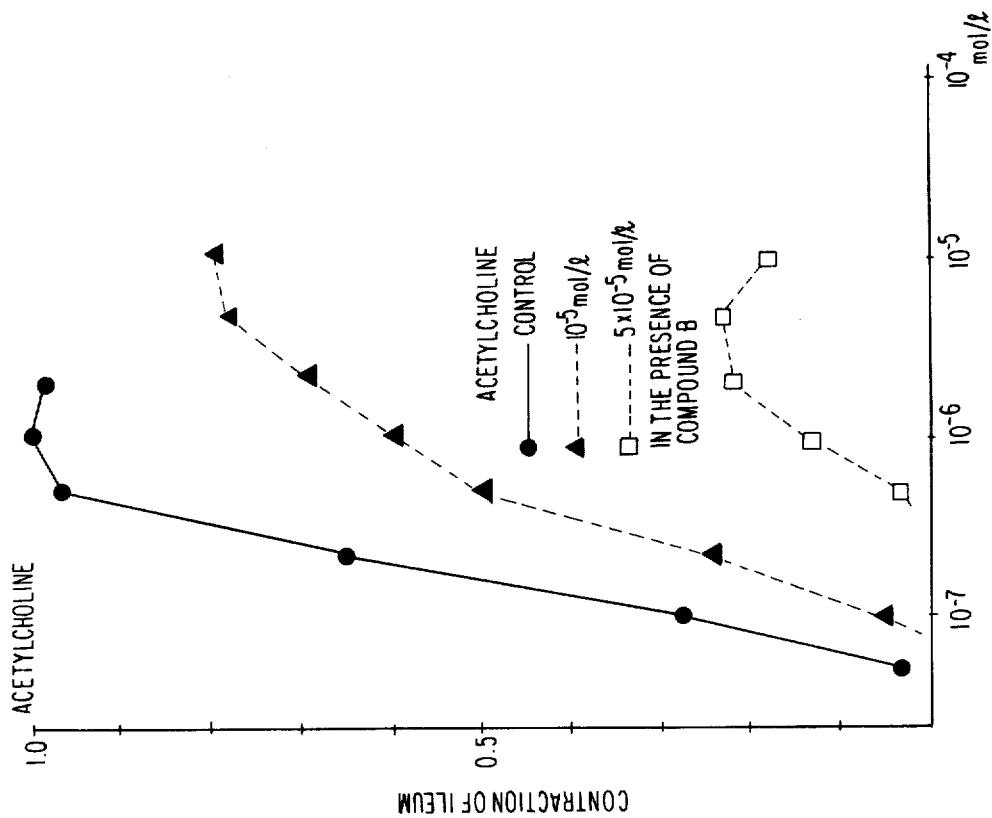
FIGS. 3(a) and 3(b) are graphs showing the anti-histamine activity and the anti-cholinergic activity of Compound B of this invention.
Figure 3A:
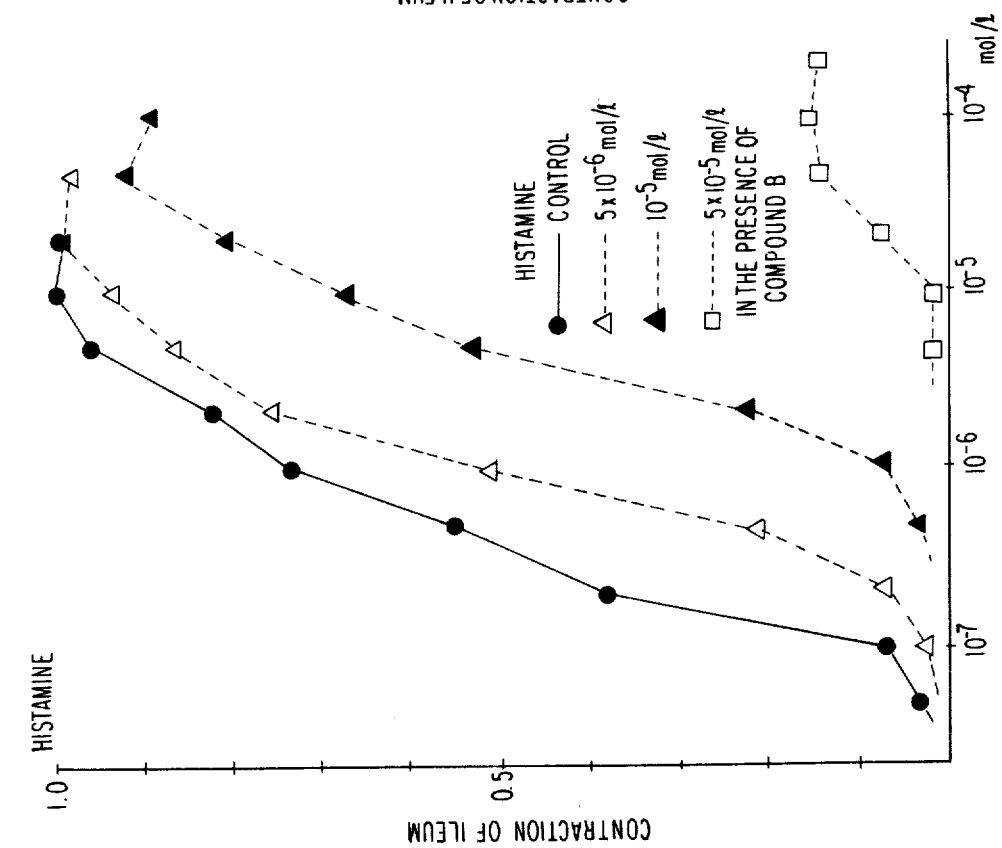
Figure 4B:
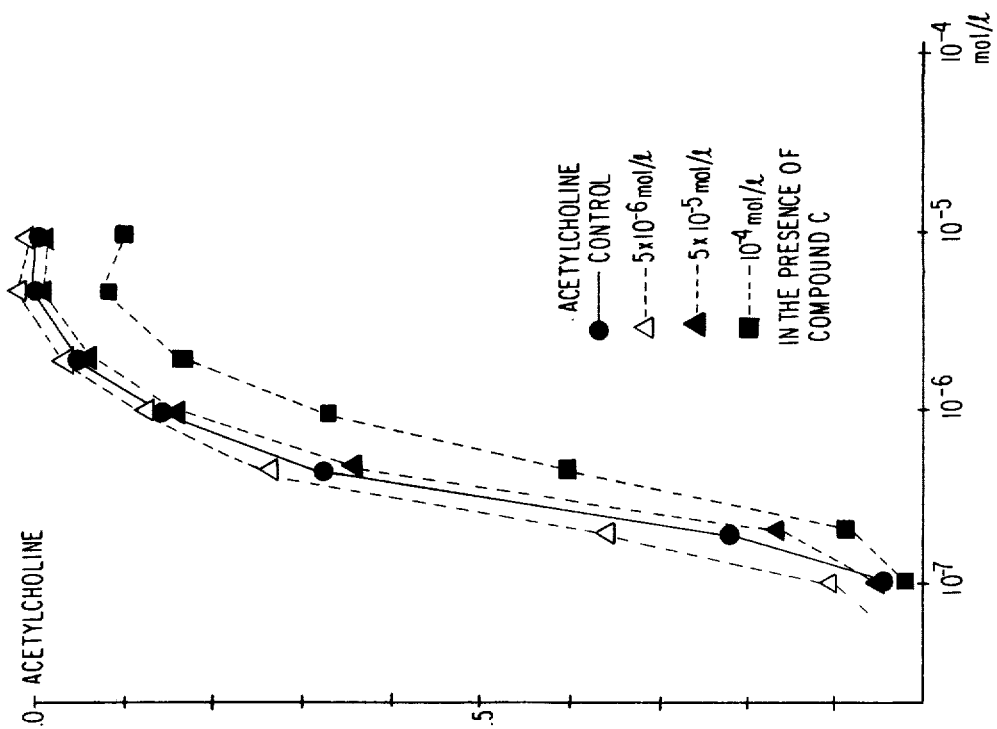
FIGS. 4(a) and 4(b) are graphs showing the anti-histamine activity and the anti-cholinergic activity of Compound C of this invention.
Figure 4A:
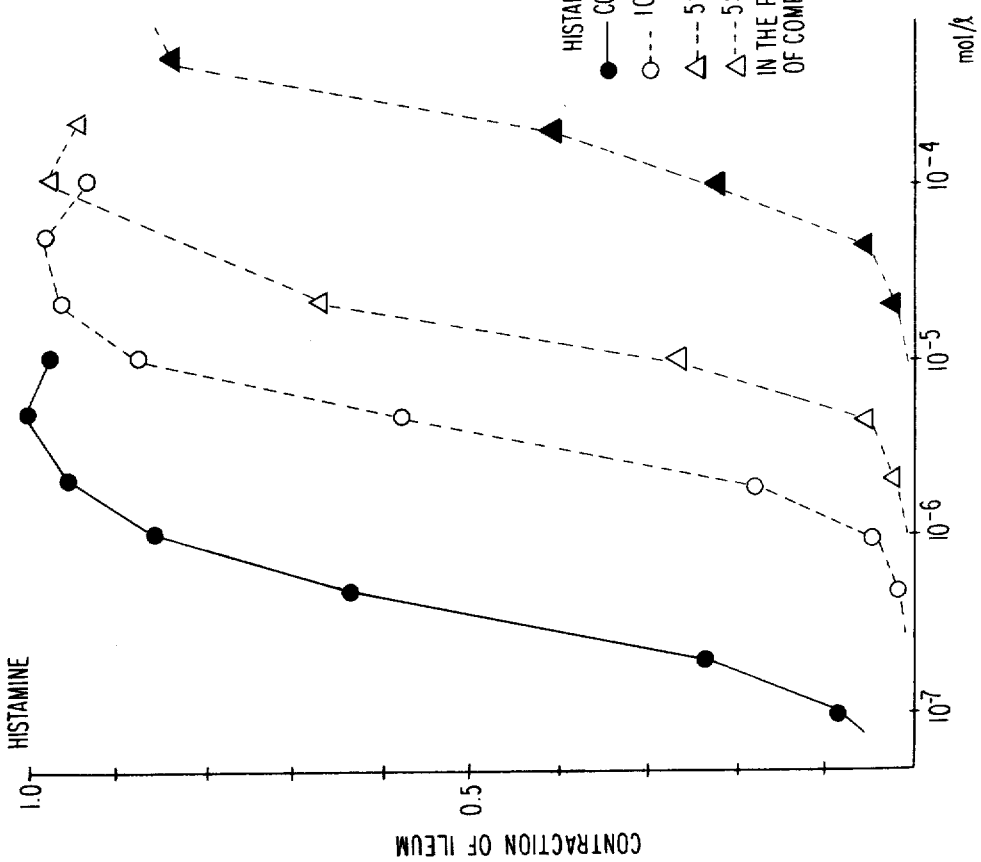

The results obtained are shown in FIG. 2(a) and FIG. 2(b) for Compound A, FIG. 3(a) and FIG. 3(b) For Compound B and FIG. 4(a) and FIG. 4(b) for Compound C. As is apparent from these figures, Compounds A, B and C shift the hitamine-induced contraction curve determined in guinea pig ileum to the right direction on the figures in parallel. This indicates that Compounds A, B, and C possess a specific anti-histamine activity. Also, Compounds A and B were found to have a non-specific anti-cholinergic activity.

Gastric Secretion Inhibitory Activity

The pylorus of Wister male rats (body weight, 180 to 200 g) fasted for 24 hours was ligated under ether anesthesia and, immediately thereafter, the test compound was administered into the duodenum. Four hours after the administration, the stomach was extracted and gastric juice was collected and centrifuged at 3,000 r.p.m. for 15 minutes. The volume of gastric juice, the pH value and the amount of output secretion were then determined with respect to the supernatant.

The results obtained are shown in Table 2 below. As is apparent from the results, Compounds A and C reduce the volume of gastric juice and the acid secretion and increase the pH value.

TABLE 2

| Compound | Dose (mg/kg) | Gastric Secretion Inhibitory Activity | | | |
|---|---|---|---|---|---|
| | | Number of Rats | Amount of Gastric Juice (ml) | pH Value | Amount of Output Secretion ($\mu$ Eq.) |
| Control | | 9 | 2.51 ± 0.32 | 1.71 ± 0.11 | 184 ± 27.2 |
| Compound A | 100 | 10 | 0.53 ± 0.12** | 3.06 ± 0.44* | 22 ± 5.9** |
| Compound C | 100 | 10 | 1.85 ± 0.35 | 1.88 ± 0.10 | 72 ± 5.3** |
| Atropine | 5 | 10 | 0.90 ± 0.09** | 2.22 ± 0.25 | 57 ± 6.0** |

*$p < 0.05$
**$p < 0.01$

Anti-ulcer Activity (i) Stress Ulcer

The test compound was administered orally to Wister male rats (body weight, 200 to 230 g) and then the rats were tied up with a steel wire and dipped in water at 23° C. in a tank to the level of the xiphisternum of rats. After allowing the rats to stand for 7 hours in water, the rats were sacrificed and the stomach was extracted. 10 ml of a 1% formalin solution was injected into the stomach cavity and the stomach was dipped in a 1% formalin solution for 15 minutes to semi-harden the stomach. The stomach was excised along the greater curvature thereof and the ulcer generated in the portion of corpus ventriculi was observed. The results obtained are shown in Table 3 below. As is apparent from the results, Compound A inhibits the ulcer generation caused by water-dipping restriction stress at the dose of 25, 50 and 100 mg, with dependency upon the dose.

TABLE 3

| Compound | Anti-ulcer Activity (Stress) | | | |
|---|---|---|---|---|
| | Dose (mg/kg) | Number of Rats | Ulcerous Index (mm) | Percent Inhibition (%) |
| Control | | 6 | 75.8 | |
| Compound A | 25 | 6 | 58.0 | 23.5 |
| Compound A | 50 | 6 | 48.2 | 36.4 |
| Compound A | 100 | 6 | 25.3 | 66.0 |
| Sulpiride* | 100 | 6 | 71.0 | — |
| Atropine | 5 | 6 | 5.3 | 93.0 |

*Sulpiride = 5-(aminosulfonyl)-N—(1-ethyl-2-pyrrolidinyl)-methyl-2-methoxybenzamide A suspension of indomechacin in 0.25% CMC was administered subcutaneously at a dose of 20 mg/kg to Wister male rats (body weight, 125 to 150 g) fasted for 24 hours. The test compound was administered orally 30 minutes before the administration of indomethacin. Seven hours after the administration of indomethacin, the rats were sacrificed by dislocation of neck, and the stomach was extracted. 7.5 ml of 1% formalin solution was injected into the stomach cavity, and the stomack was hardened. The linear-type ulcer generated in the mucous membrane of the stomach was then observed.

The results obtained are shown in Table 4. As is apparent from the results, Compounds B and D inhibit the indomethacin-induced ulcer at a dose of 50 mg/kg.

TABLE 4

| Compound | Anti-ulcer Activity (Indomethacin) | | | |
|---|---|---|---|---|
| | Dose (mg/kg) | Number of Rats | Ulcerous Index (mm) | Percent Inhibition (%) |
| Control | | 8 | 15.4 | |
| Compound B | 50 | 8 | 6.0 | 61.0 |
| Compound D | 50 | 8 | 4.1 | 73.0 |
| Sucralfate* | 300 | 2.9 | 81.1 | |

*Sucralfate = basic aluminum sucrose sulfate

Acute Toxicity

The test compound was administered to ddy male mice (body weight, 20 to 25 g) fasted overnight before administration. After administration, general conditions of mice were observed for 7 days and 50% lethal dose LD$_{50}$ (mg/kg) was determined. The results obtained are shown in Table 5 below.

TABLE 5

| Acute Toxicity | |
|---|---|
| Compound | LD$_{50}$ (mg/kg) |
| Compound A | 662 |
| Compound B | 195 |
| Compound C | 699 |
| Compound D | 505 |

PREPARATION EXAMPLES

| 1. | Granules | |
|---|---|---|
| | Compound A | 200 mg |

-continued

| | | |
|---|---|---|
| Lactose | 500 mg | |
| Corn Starch | 280 mg | |
| Hydroxypropylcellulose | 20 mg | |
| | 1,000 mg per pack | |

The granule preparation was prepared in a conventional manner using the above formulation.

| 2. | Tablets | |
|---|---|---|
| | Compound B | 100 mg |
| | Lactose | 85 mg |
| | Crystalline Cellulose | 50 mg |
| | Hydroxypropylcellulose | 30 mg |
| | Talc | 4 mg |
| | Magnesium Stearate | 1 mg |
| | | 270 mg per tablet |

The tablet preparation was prepared in a conventional manner using the above formulation.

| 3. | Capsules | |
|---|---|---|
| | Compound C | 200 mg |
| | Lactose | 100 mg |
| | Crystalline Cellulose | 18 mg |
| | Magnesium Stearate | 2 mg |
| | | 400 mg per capsule |

The tablet preparation was prepared in a conventional manner using the above formulation.

As described before, some of the starting materials having the formula (II) are novel compounds. The preparations of typical examples of the novel starting materials are described in the following Reference Examples.

REFERENCE EXAMPLE 1

20 g of ethyl p-chlorophenyl acetate, 10 g of sodium ethoxide and 15 g of ethyl formate were added in that order to 200 ml of diethyl ether and the mixture was stirred for 16 hours at room temperature. Thereafter, water in an equal amount to the reaction mixture was added to the reaction mixture and, after thoroughly shaking, the aqueous layer was separated. The aqueous layer was rendered neutral with 2 N hydrochloric acid and the liberated oily substance was extracted with dichloromethane. The extract was washed with water and the solvent was distilled off to obtain 14.2 g of ethyl p-chlorophenyl-(α-formyl)acetate having a melting point of 50° C.

Then, 14.2 g of ethyl p-chlorophenyl-(α-formyl)acetate and 6.5 g of urethane were added to 50 ml of toluene containing 0.3 ml of concentrated sulfuric acid, and the mixture was heated at reflux while distilling out water which was formed during the reaction until no further water was distilled out. Thereafter, the solvent was distilled off, and the residue was extracted with diethyl ether while hot. The solvent was distilled off from the extract to obtain 13.7 g of ethyl p-chlorophenyl-(α-ethoxycarbonylaminomethylene)acetate having a melting point of 72° C.

Then, 13.7 g of ethyl p-chlorophenyl-(α-ethoxycarbonylaminomethylene)acetate was added to 50 ml of diphenyl ether and the mixture was heated at reflux for 3 hours. After cooling, benzene and petroleum ether were added to the reaction mixture, and the precipitated crystals were filtered and recrystallized from a mixture of dimethylformamide and ethanol to obtain 7 g of 7-chloro-4-ethoxycarbonyl-1(2H)-isoquinolone having a melting point of 243° C. as colorless prisms.

Elementary Analysis: Calcd for $C_{12}H_{10}ClNO_3=251.671$: C, 57.27; H, 4.01; N, 5.57 (%). Found: C, 57.36; H, 4.05; N, 5.53 (%).

REFERENCE EXAMPLE 2

The procedure described in Reference Example 1 was repeated but using ethyl p-methoxyphenylacetate as a starting material instead of the ethyl p-chlorophenylacetate, and the resulting crystals were recrystallized from a mixture of dimethylformamide and ethanol to obtain 4-ethoxycarbonyl-7-methoxy-1(2H)-isoquinoline having a melting point of 191° C. as colorless prisms. Yield, 64%.

Elementary Analysis: Calcd for $C_{13}H_{13}NO_4=247.253$: C, 63.15; H, 5.30; N, 5.66 (%). Found: C, 63.27; H, 5.28; N, 5.72 (%).

REFERENCE EXAMPLE 3

The procedure described in Reference Example 1 was repeated but using p-methoxyphenylacetonitrile as a starting material instead of the ethyl p-chlorophenylacetate, and the resulting crystals were recrystallized from a mixture of dimethylformamide and ethanol to obtain 4-cyano-7-methoxy-1(2H)-isoquinolone having a melting point of 264° C. Yield, 58%.

Elementary Analysis: Calcd for $C_{11}H_8N_2O_2=200.199$: C, 66.00; H, 4.03; N, 13.99 (%). Found: C, 66.16; H, 4.20; N, 13.88 (%).

REFERENCE EXAMPLE 4

A mixture of 19 g of 4-carboxy-1(2H)-isoquinolone, 10 ml of concentrated sulfuric acid and 1 liter of n-butanol was heated at reflux for 20 hours. The solvent was distilled off and petroleum ether was added to the residue, followed by allowing the mixture to stand. The solidified substance was separated by filtration and recrystallized from a mixture of n-butanol and petroleum ether to obtain 17 g of 4-n-butoxycarbonyl-1(2H)-isoquinoline as colorless needles having a melting point of 170° C.

Elementary Analysis: Calcd for $C_{14}H_{15}NO_3=245.281$: C, 68.56; H, 6.16; N, 5.71 (%). Found: C, 68.62; H, 6.11; N, 5.58 (%).

What is claimed is:

1. 1(2H)-Isoquinolone compounds represented by the formula (I)

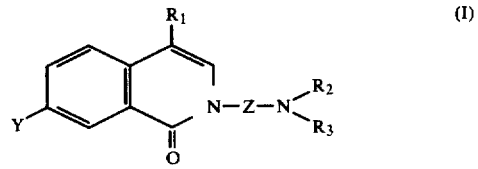

(I)

wherein Y represents hydrogen, chlorine or a methoxy group, Z represents a straight chain or branched chain divalent saturated aliphatic hydrocarbon group having 2 to 4 carbon atoms, $R_1$ represents a cyano group, a lower alkoxycarbonyl group, a carbamoyl group, N-alkylcarbamoyl having 1 to 4 carbon atoms in the alkyl moiety, N,N-dialkylcarbamoyl having 1 to 4 carbon atoms in each alkyl moiety, 4-methylpiperazinocarbonyl or morpholinocarbonyl, a phenyl group or halophenyl or alkoxyphenyl having 1 to 4 carbon atoms in the alkoxy moiety, $R_2$ represents hydrogen or a lower alkyl group, $R_3$ represents a lower alkyl group, or $R_2$ and $R_3$ can form, when taken together with nitrogen atom to which they are attached, pyrrolidino, piperidino, 4-methylpiperazino, 4-hydroxyethylpiperazino or morpholino, and the pharmaceutically acceptable acid addition salts thereof.

2. 2-(3-N,N-Dimethylaminopropyl)-4-phenyl-1(2H)-isoquinolone or the acid addition salt thereof according to claim 1.

3. 2-(2-N,N-Dimethylaminoethyl-4-phenyl-1(2H)-isoquinolone or the acid addition salt thereof according to claim 1.

4. 4-Cyano-2-(3-N,N-dimethylaminopropyl)-1(2H)-isoquinolone and the acid addition salt thereof according to claim 1.

5. 2-(2-N,N-Dimethylaminopropyl)-4-phenyl-1(2H)-isoquinolone and the acid addition salt thereof according to claim 1.

* * * * *